US00PP35505P2

(12) United States Plant Patent
Armenta Robles et al.

(10) Patent No.: US PP35,505 P2
(45) Date of Patent: Nov. 28, 2023

(54) MANGO TREE NAMED 'KANKUN'

(50) Latin Name: ***Mangifera indica* L.**
Varietal Denomination: Kankun

(71) Applicant: Sun World International, LLC, Bakersfield, CA (US)

(72) Inventors: Jesus Armenta Robles, Mazatlán (MX); Jose Antonio Garzon Tiznado, Mazatlán (MX)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 17/993,749

(22) Filed: Nov. 23, 2022

Related U.S. Application Data

(60) Provisional application No. 63/380,930, filed on Oct. 25, 2022.

(51) Int. Cl.
*A01H 5/08* (2018.01)
*A01H 6/00* (2018.01)

(52) U.S. Cl.
USPC ..... Plt./159

(58) Field of Classification Search
USPC ..... Plt./159
CPC ..... A01H 5/08; A01H 5/00; A01H 6/00
See application file for complete search history.

(56) References Cited

PUBLICATIONS

Upov Pluto Feb. 13, 2023 retrieved on Feb. 13, 2023 at https://pluto.upov.int/result, one page (Year: 2023).*
Estados Unidos Mexicanos Secretaria de Agricultura y Desarrollo Rural, Plant Breeder's Right Certificate of Grant for Mango Kankun, MX2819 filed on Oct. 26, 2021, 2 pp. (Year: 2021).*
Innovaciones Vegetales 2021 retrieved on Jun. 27, 2023 at https://www.gob.mx/snics/articulos/catalogo-de-innovaciones-vegetales-2021-292193?idiom=es, cover page and p. 146. (Year: 2023).*
English translation of Innovaciones Vegetales 2021, 2 pp. total (Year: 2023).*

* cited by examiner

*Primary Examiner* — June Hwu
(74) *Attorney, Agent, or Firm* — Knobbe, Martens, Olson & Bear, LLP

(57) ABSTRACT

The new mango tree variety 'Kankun' is characterized by having medium-size, oblong-ovoid, Yellow-Orange fruit with a long shelf life and an early harvest.

18 Drawing Sheets

Latin name of the genus and species claimed: *Mangifera indica* L.

Variety denomination: 'KANKUN'.

BACKGROUND AND SUMMARY OF THE INVENTION

This invention relates to the discovery and asexual propagation of a new and distinct variety of mango, *Mangifera indica* L. 'Kankun'. The variety 'Kankun' was originated by hybridization and selection of segregants and was first selected in 2014 by Jesus Armenta Robles and Jose Antonio Garzon Tiznado. The new variety as first evaluated by Jesus Armenta Robles and Jose Antonio Garzon Tiznado near Sinaloa, Mexico.

The parent varieties are TommyKent (unpatented) and Ataulfo (unpatented). The parent varieties were first crossed during the period December 2009 to January 2010 using bees. The resulting fruit was planted and fruit from the F1 generation was selected in July-August 2010. F1 fruit was planted in October 2010 and 55 F2 individuals were selected in 2012. 5 of those F2 plants with early harvest fruit were selected in 2013 and the Kankun variety was selected from among those in 2014. The new mango variety 'Kankun' was first asexually propagated by Jesus Armenta Robles and Jose Antonio Garzon Tiznado near Sinaloa, Mexico in 2014 by grafting.

The new variety 'Kankun' is characterized by having medium-size, oblong-ovoid, Yellow-Orange fruit with a long shelf life and early harvest.

The new variety 'Kankun' differs from its seed parent 'TommyKent' (unpatented) in that the new variety has an early harvest and the fruit has a high amount of fiber attached to the stone, compared to a mid-season harvest and low fiber amount attached to the stone for 'TommyKent.' Additionally, the stone of new variety 'Kankun' has a grooved surface relief, compared to ridged surface relief for 'TommyKent.' Furthermore, the new variety 'Kankun' has medium-size, oblong-ovoid fruit, compared to the large-size and oblong fruit of 'TommyKent'. Lastly, the mature fruit of the new variety 'Kankun' has Yellow-Green skin color, compared to a Red skin color for the mature fruit of 'TommyKent'.

The new variety 'Kankun' resembles its pollen parent 'Ataulfo' (unpatented) in that both have an early harvest; however the new variety is distinguished from its pollen parent in that the new variety 'Kankun' has oblong-ovoid shaped Yellow-Orange colored fruit, compared to elongated kidney shaped Yellow colored fruit for 'Ataulfo'.

The new variety 'Kankun' resembles the variety 'Tommy Atkins' (unpatented) in that both have medium-size fruit and the mature fruit has small size lenticels with medium density. Further, the fruit of the new variety 'Kankun' and the fruit of 'Tommy Atkins' have an early harvest. The new variety 'Kankun' differs from 'Tommy Atkins' in that the new variety has Yellow-Orange colored fruit with a high amount of fiber attached to the stone, compared to Orange-Purple colored fruit with a low amount of fiber attached to the stone for 'Tommy Atkins'. Additionally, the stone of the new variety 'Kankun' has a grooved surface relief, compared to a ridged surface relief for 'Tommy Atkins'.

The new variety 'Kankun' resembles the variety 'Keitt' (unpatented) in that both have medium-size fruit. The new variety 'Kankun' differs from 'Keitt' in that the new variety has an early harvest and the fruit has a high amount of fiber attached to the stone, compared to a late season harvest and low amount of fiber attached to the stone for 'Keitt'. Additionally, the stone of the new variety 'Kankun' has a grooved surface relief, compared to a ridged surface relief for 'Keitt'.

The new variety 'Kankun' resembles the variety 'Haden' (unpatented) in that both have medium-size fruit. The new variety 'Kankun' differs from 'Haden' in that the new variety has an early harvest and the fruit has a high amount of fiber attached to the stone, compared to a mid-season harvest and low amount of fiber attached to the stone for 'Haden'. Further, the fruit of the new variety 'Kankun' has Red-Orange skin, compared to Yellow-Red skin for 'Haden'.

The new variety 'Kankun' has been shown to maintain its distinguishing characteristics through successive asexual propagations by, for example, cuttings and grafting.

BRIEF DESCRIPTION OF THE DRAWING

The accompanying color photographic illustrations were taken shortly after the fruit was picked from 3 to 4 year old plants and the colors are as nearly true as is reasonably possible in a color representation of this type.

DETAILED DESCRIPTION OF THE PREFERRED EMBODIMENT

Figure 1:
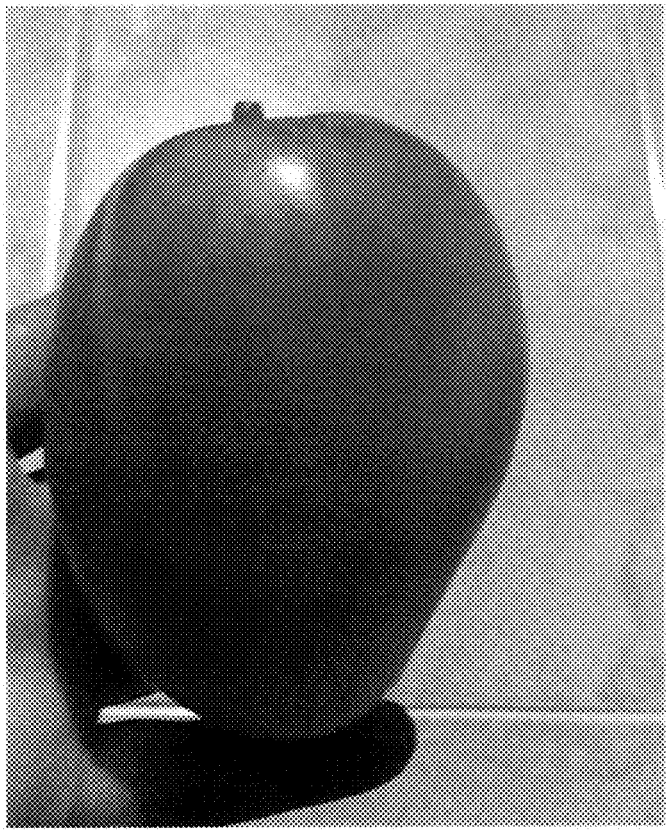
FIG. 1, FIG. 2 and FIG. 3 show the fruit of the new variety 'Kankun', illustrating the Yellow-Orange color of mature fruit.
Figure 2:
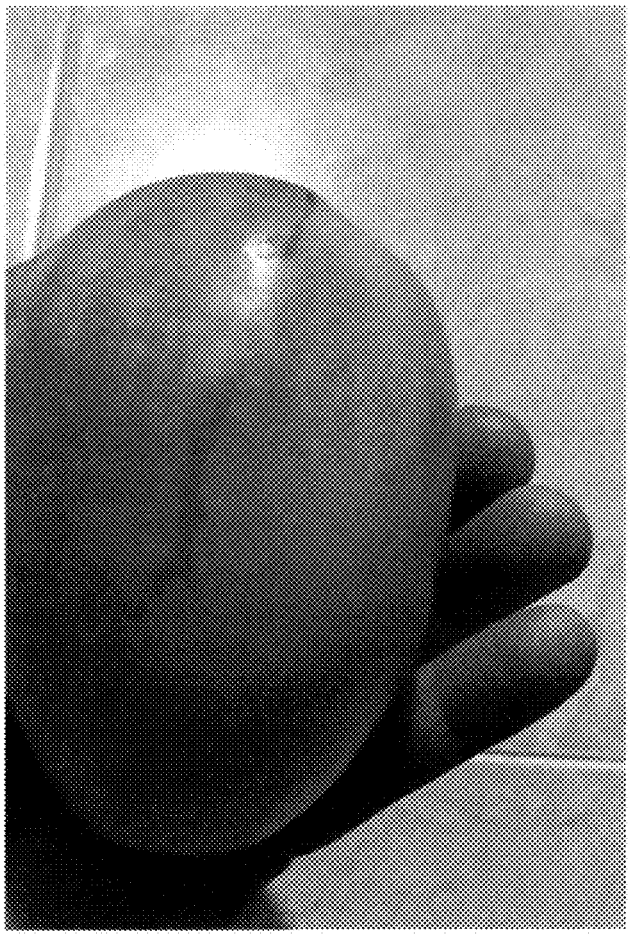
Figure 3:
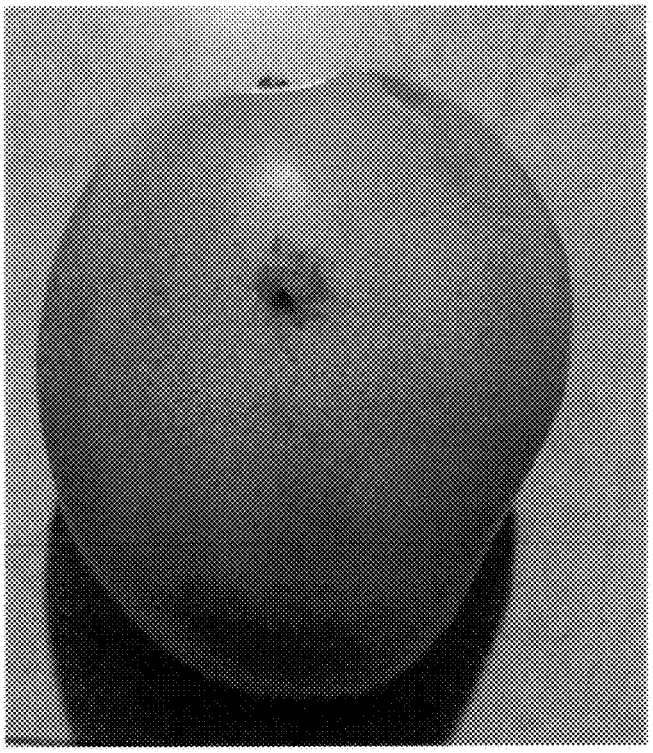
Figure 4:
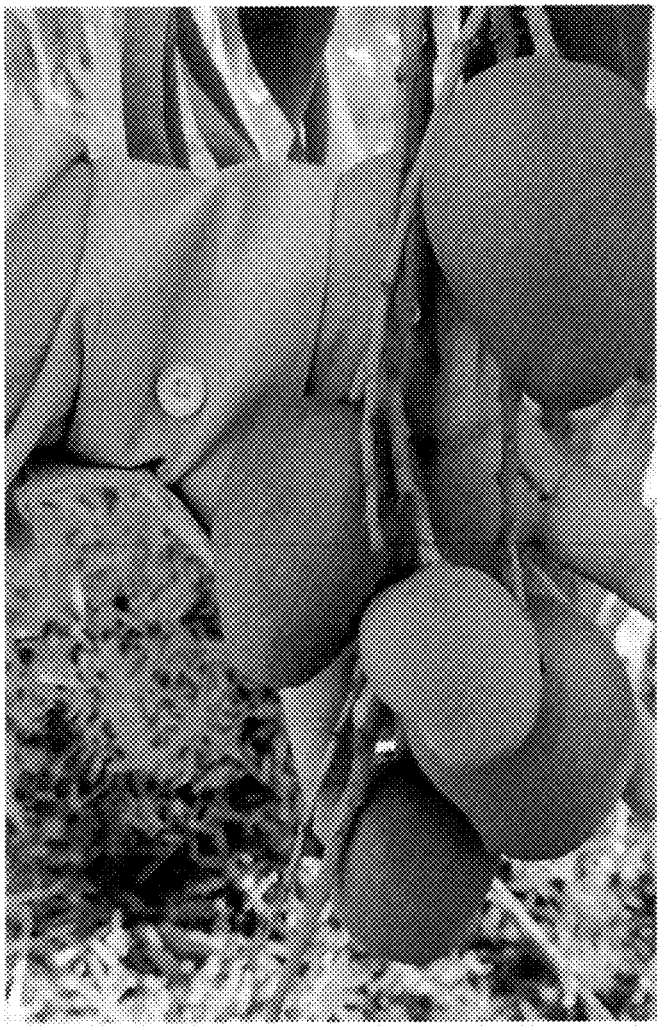
FIG. 4 shows the fruit of the new variety 'Kankun', illustrating the Red-Green color of immature fruit still hanging from the tree.
Figure 5:
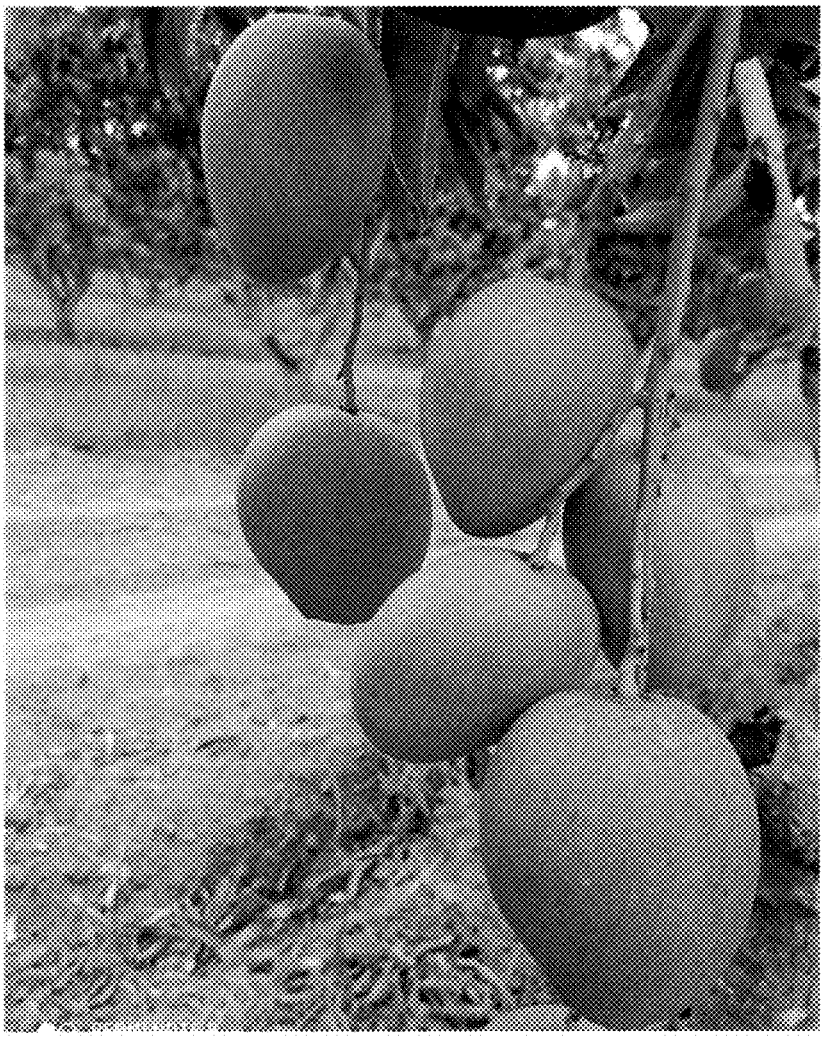
FIG. 5, FIG. 6 and FIG. 7 show the immature fruit of the new variety 'Kankun' still hanging from the tree.
Figure 6:
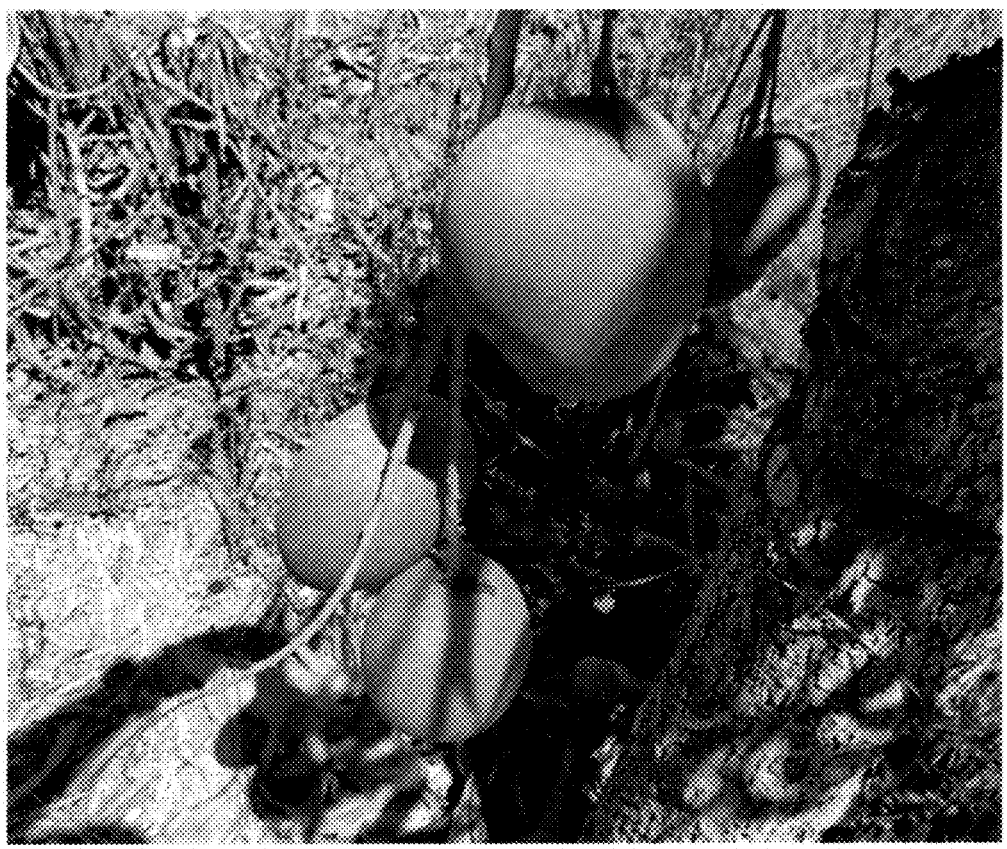
Figure 7:
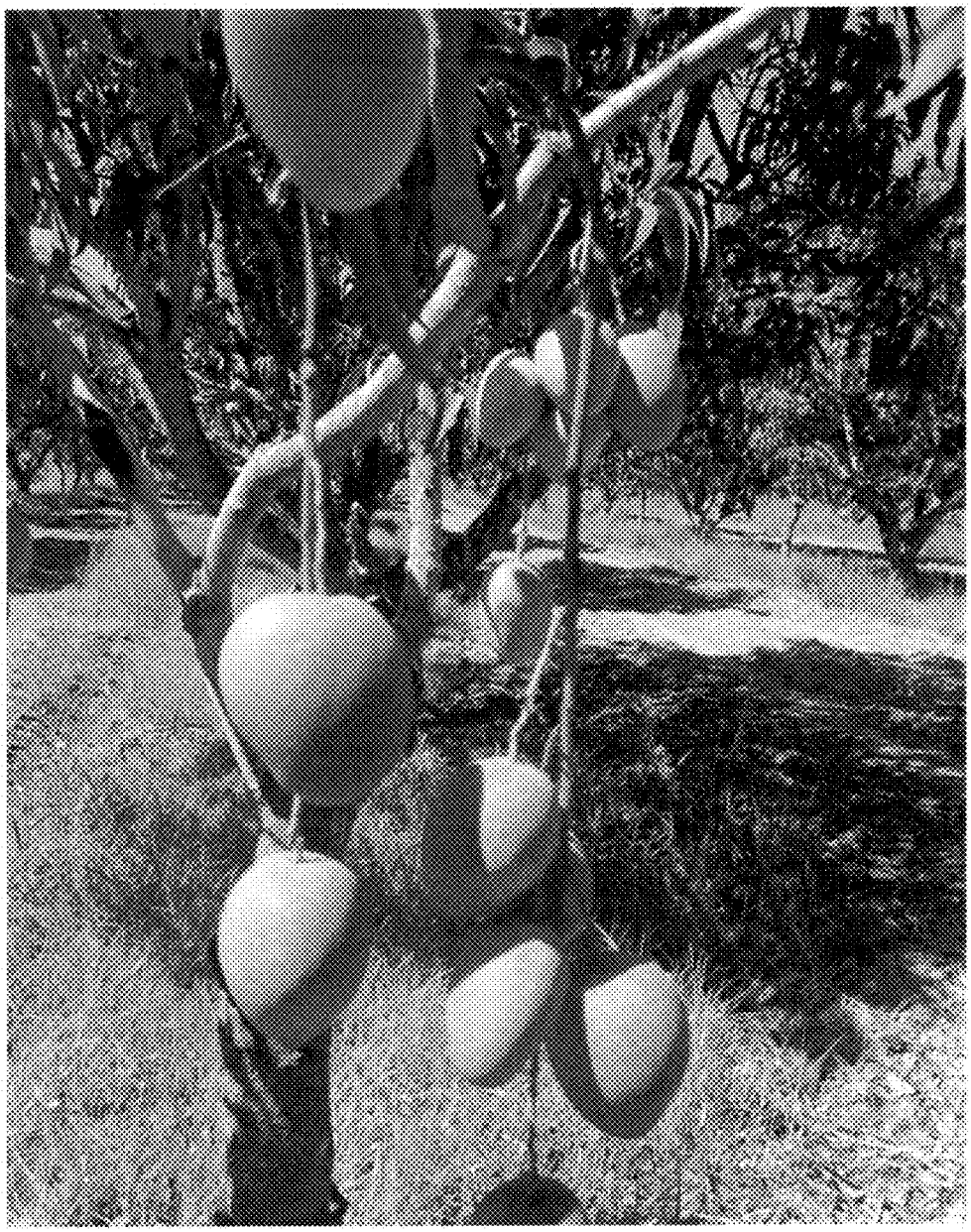
Figure 8:
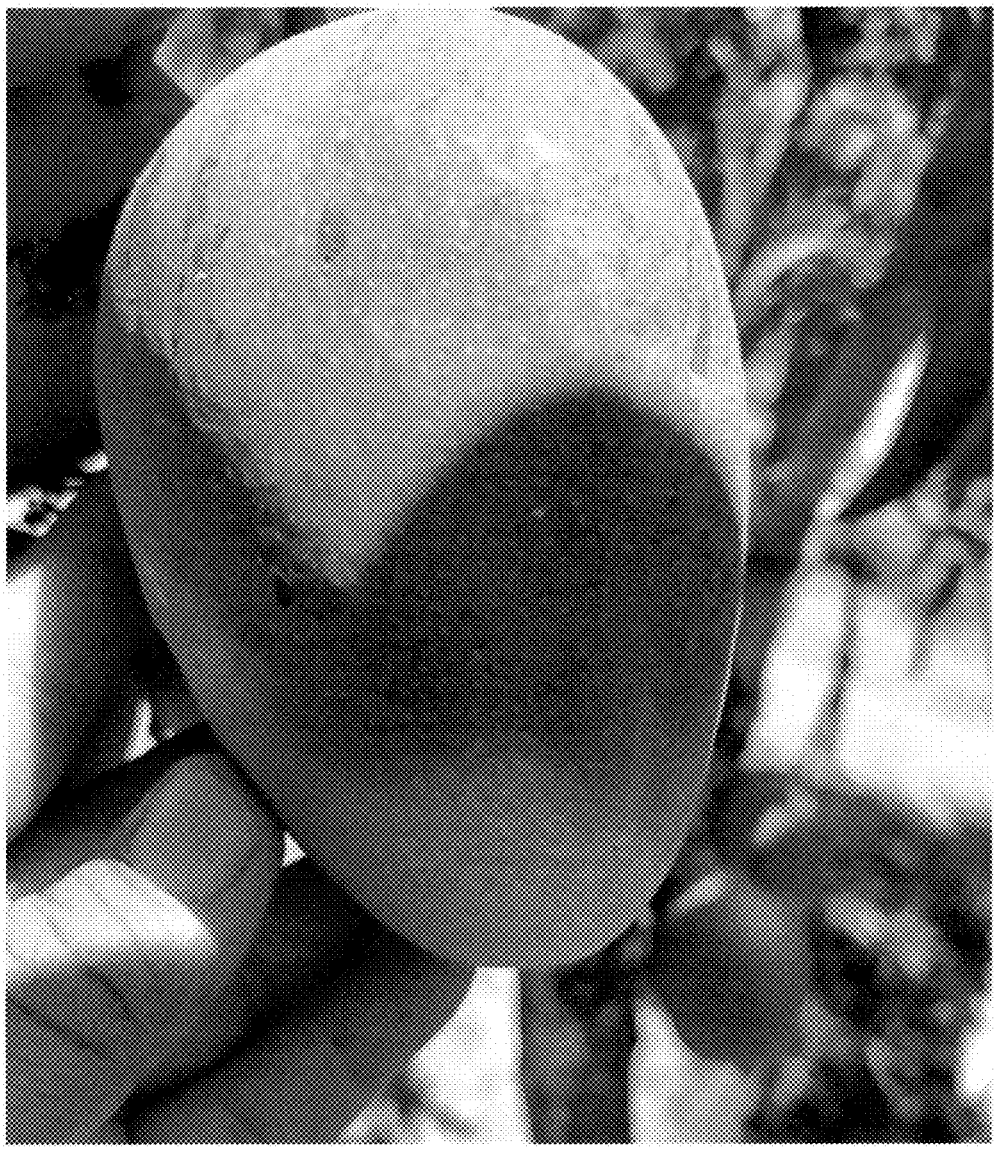
FIG. 8 and FIG. 9 show close-up views of the fruit of the new variety 'Kankun'.
Figure 9:
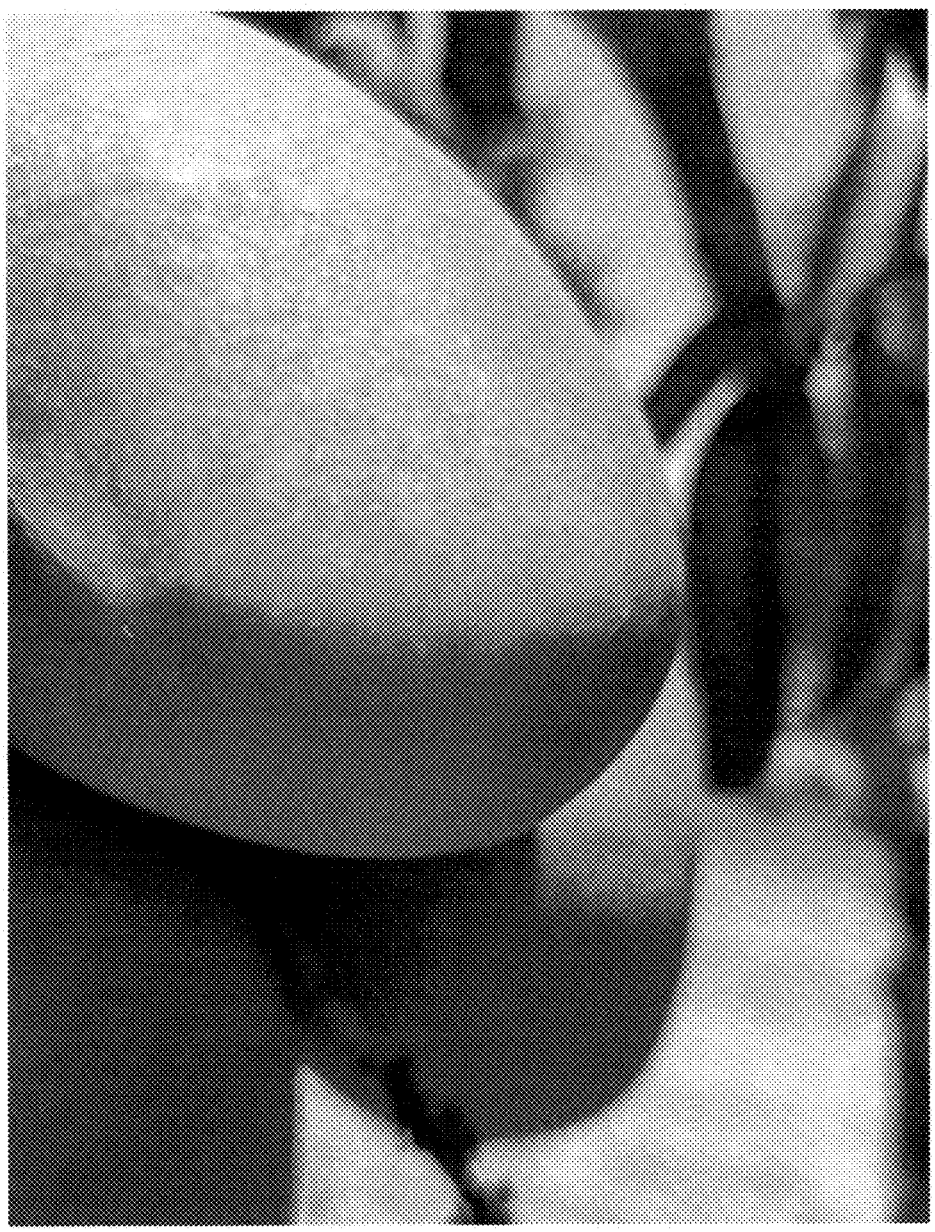
Figure 10:
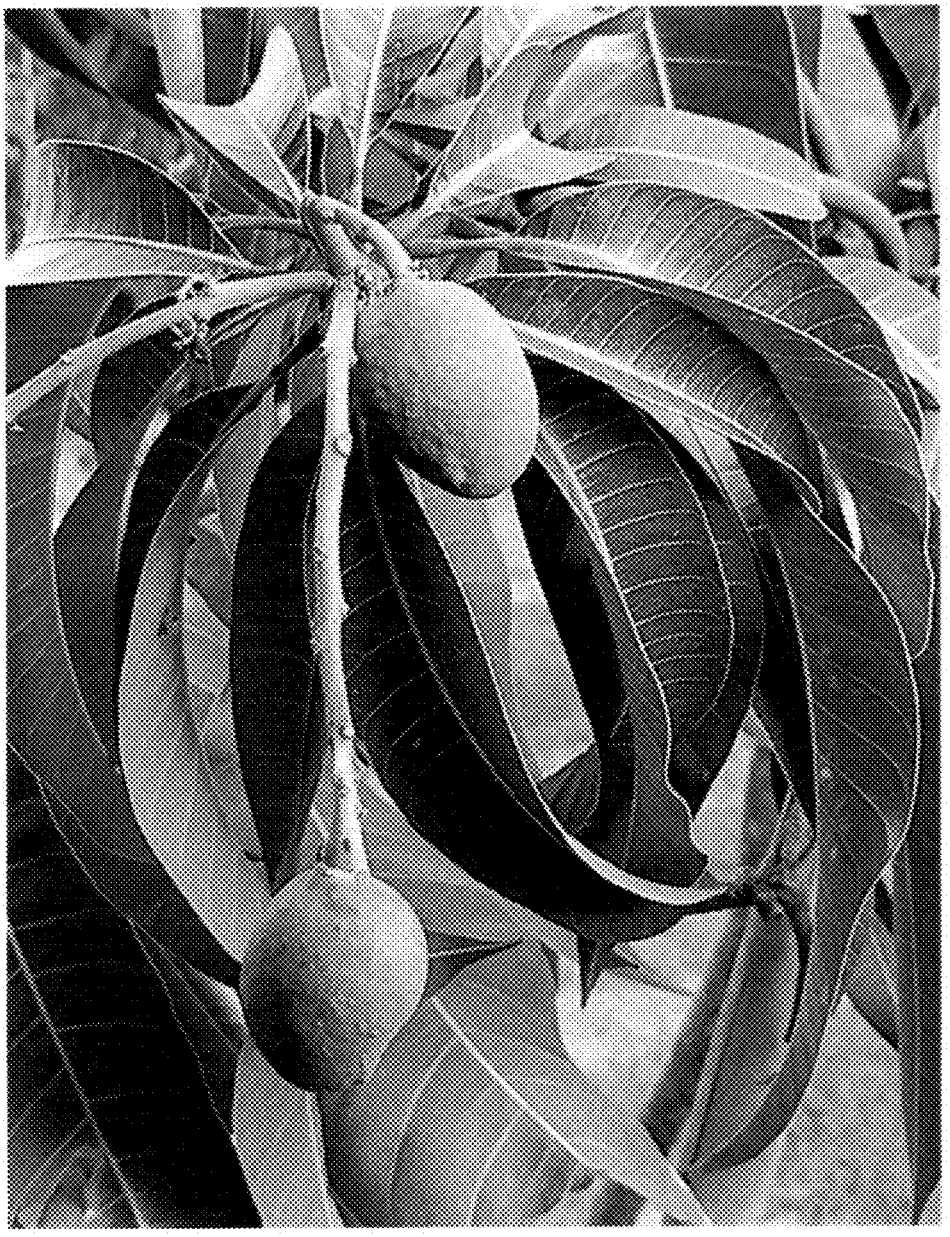
FIG. 10 shows the immature fruit of the new variety 'Kankun'.
Figure 11:
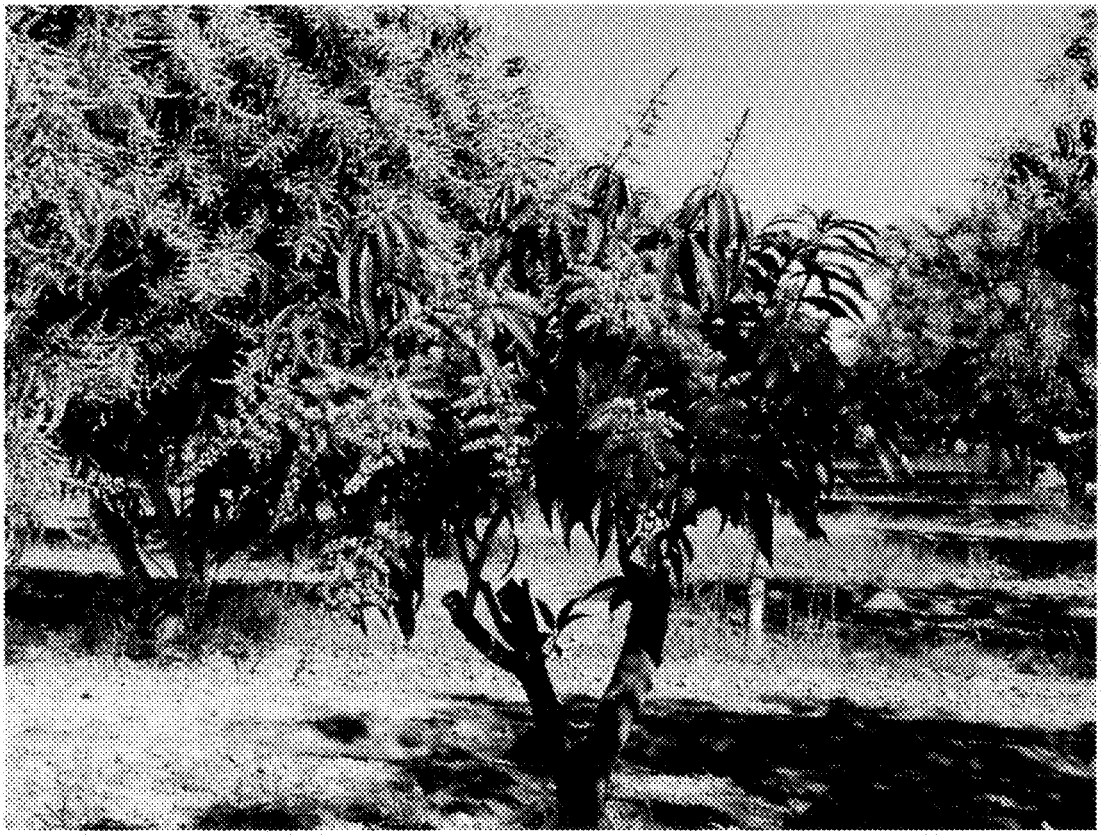
FIG. 11 and FIG. 12 show aspects of the mango tree of the new variety 'Kankun'.
Figure 12:
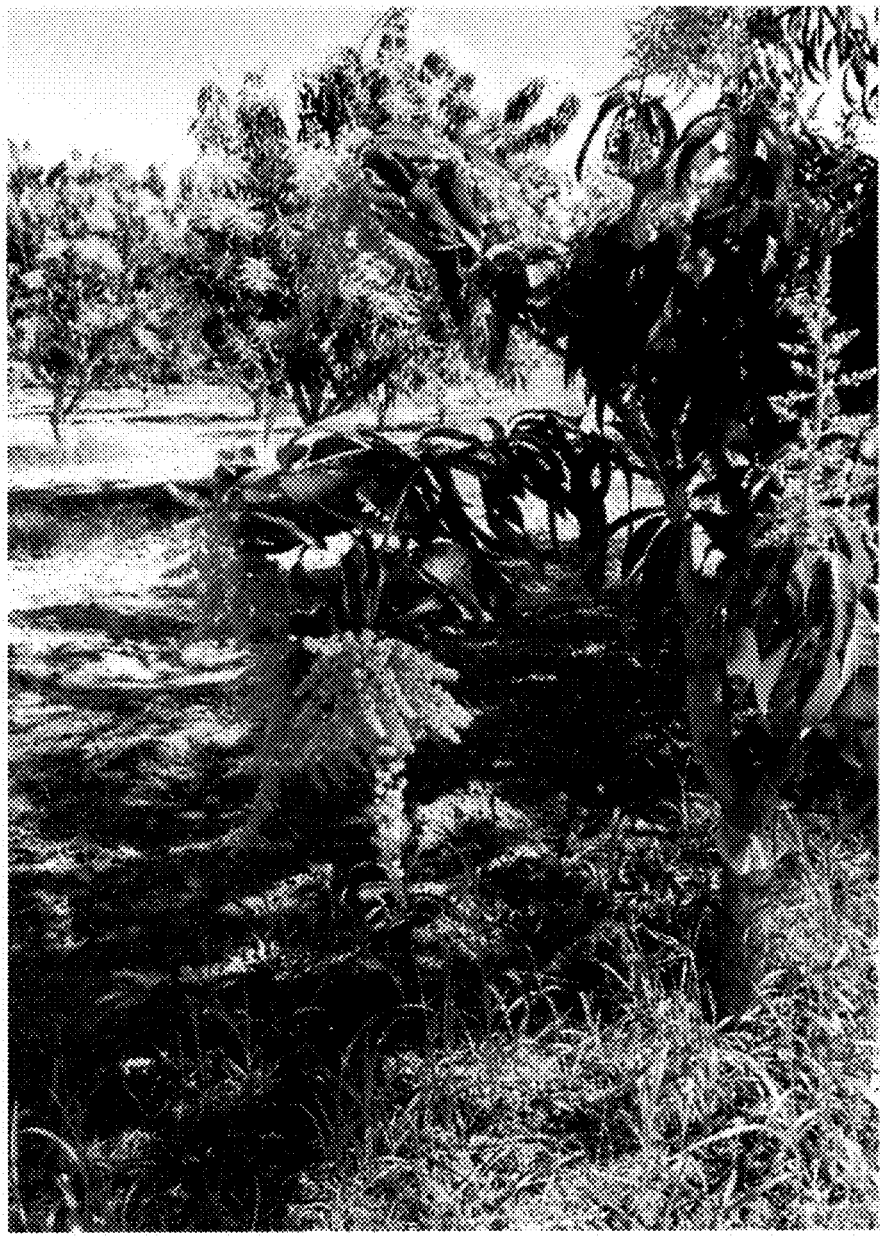
Figure 13:
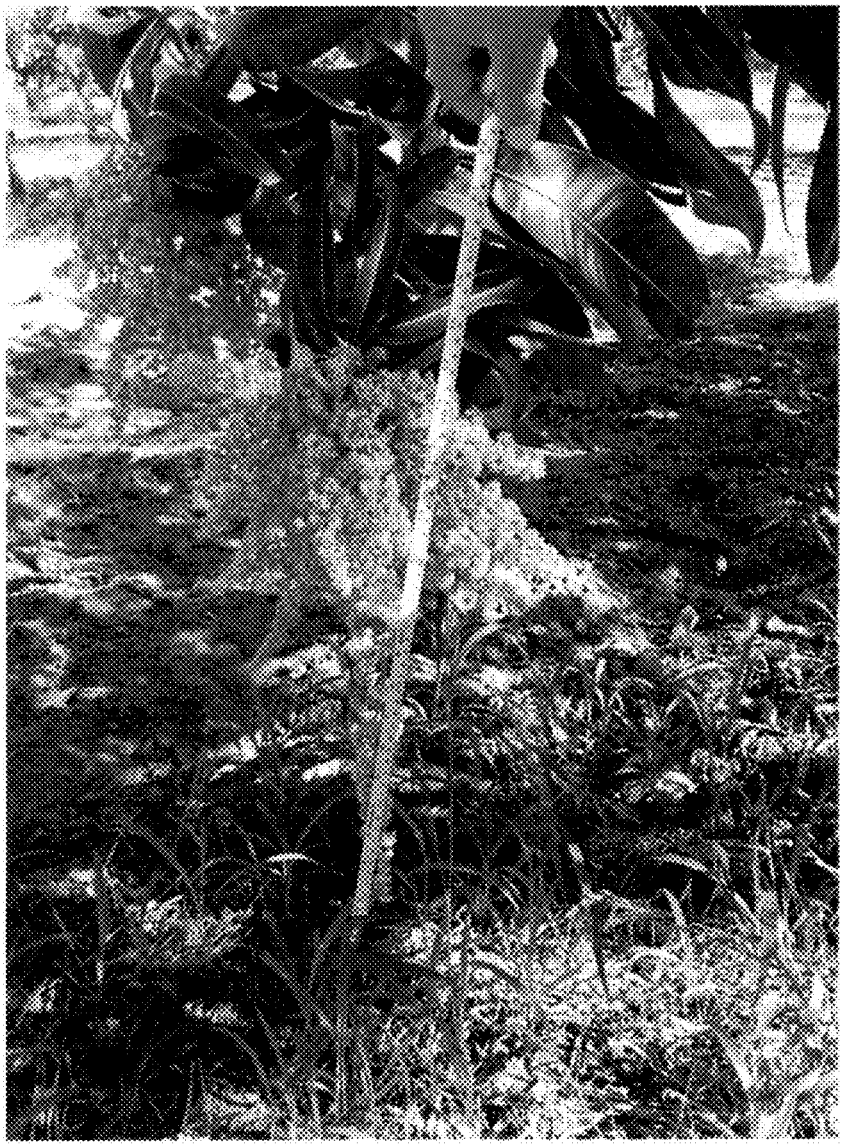
FIG. 13, FIG. 14, FIG. 15 and FIG. 16 show the flowers of the new variety 'Kankun'.
Figure 14:
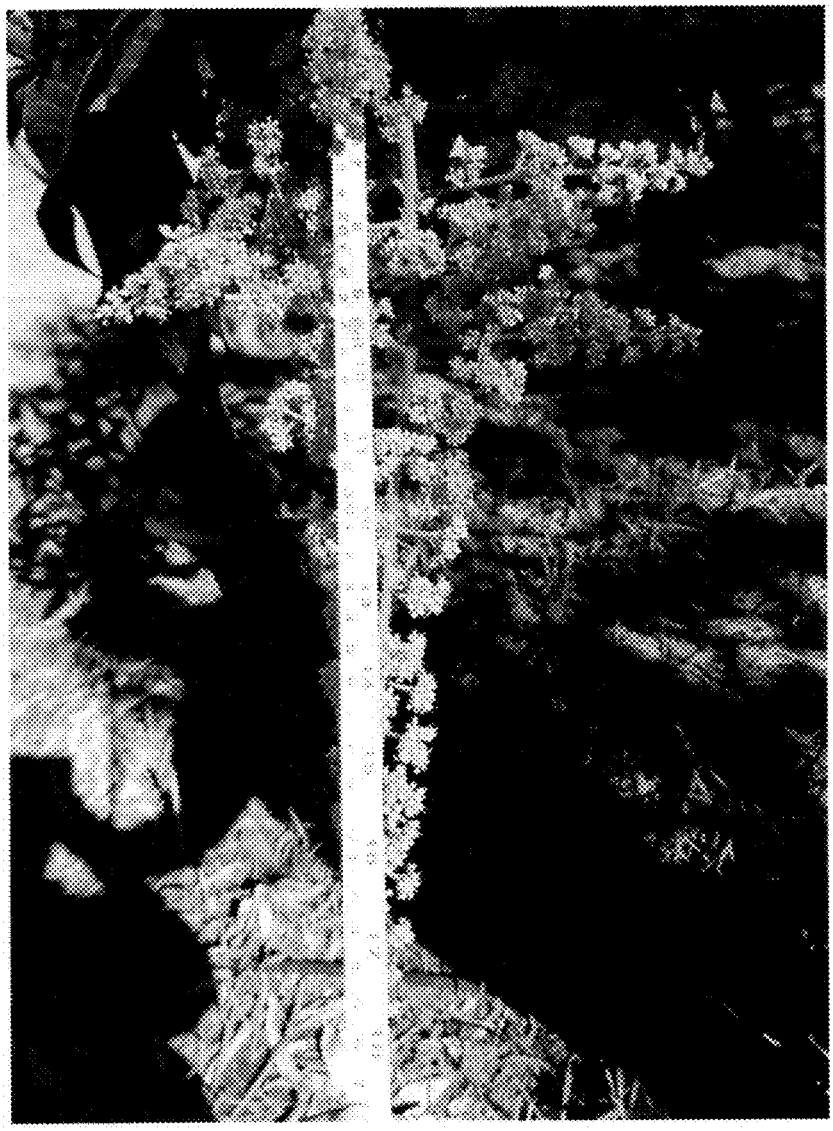
Figure 15:
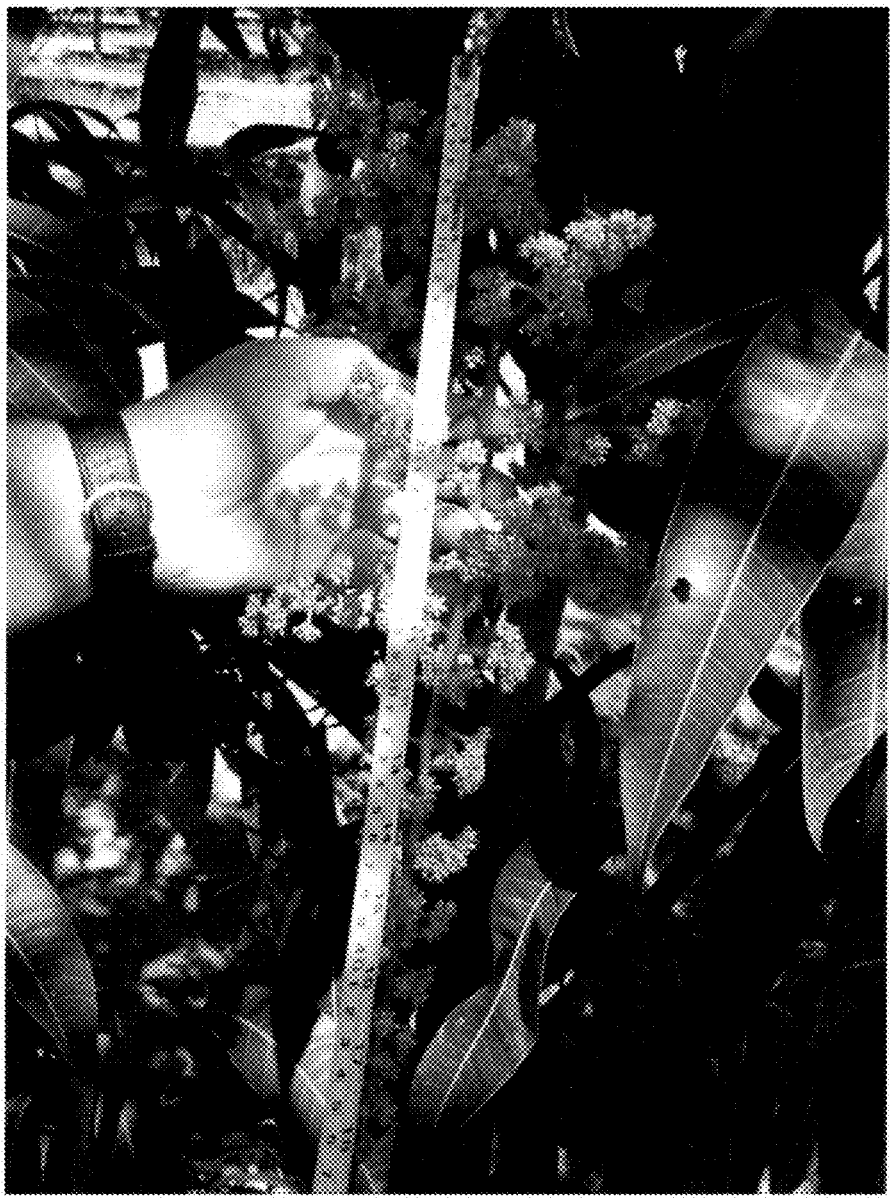
Figure 16:
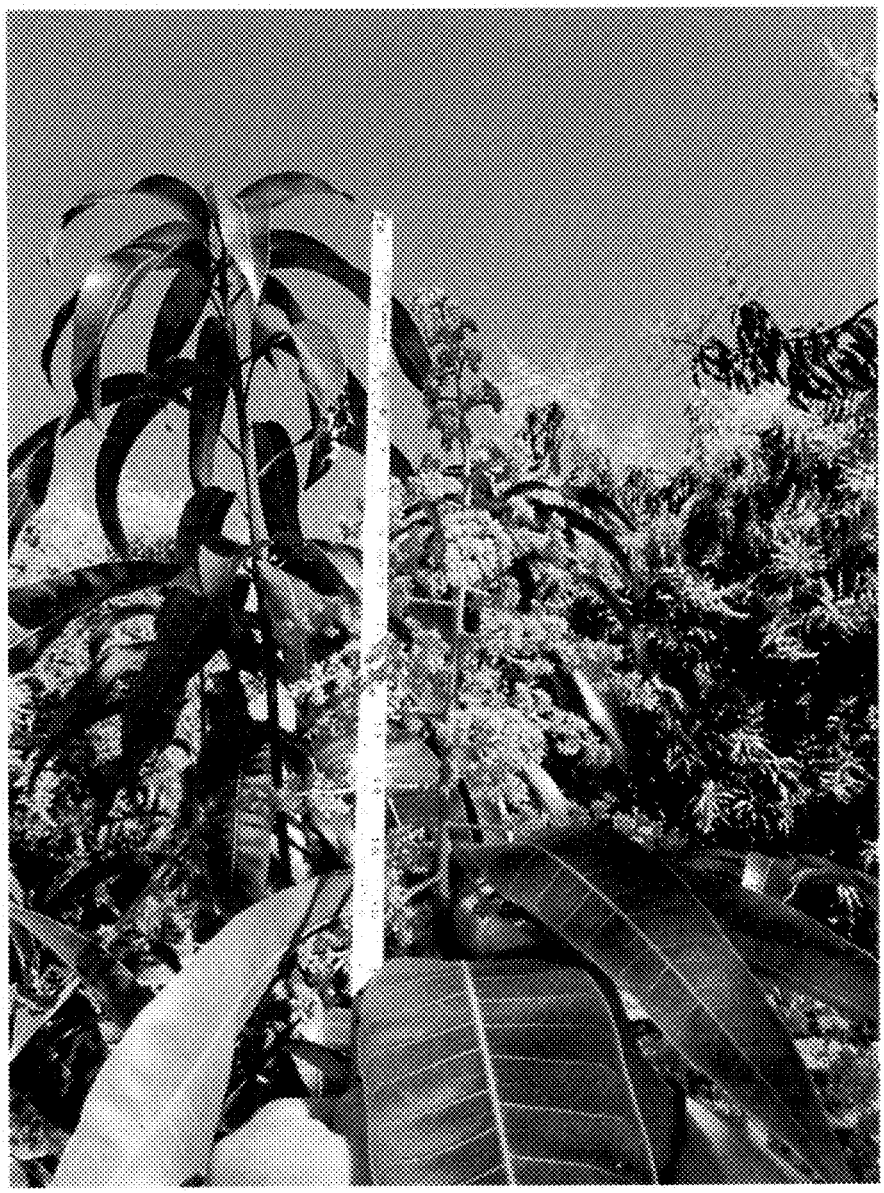
Figure 17:
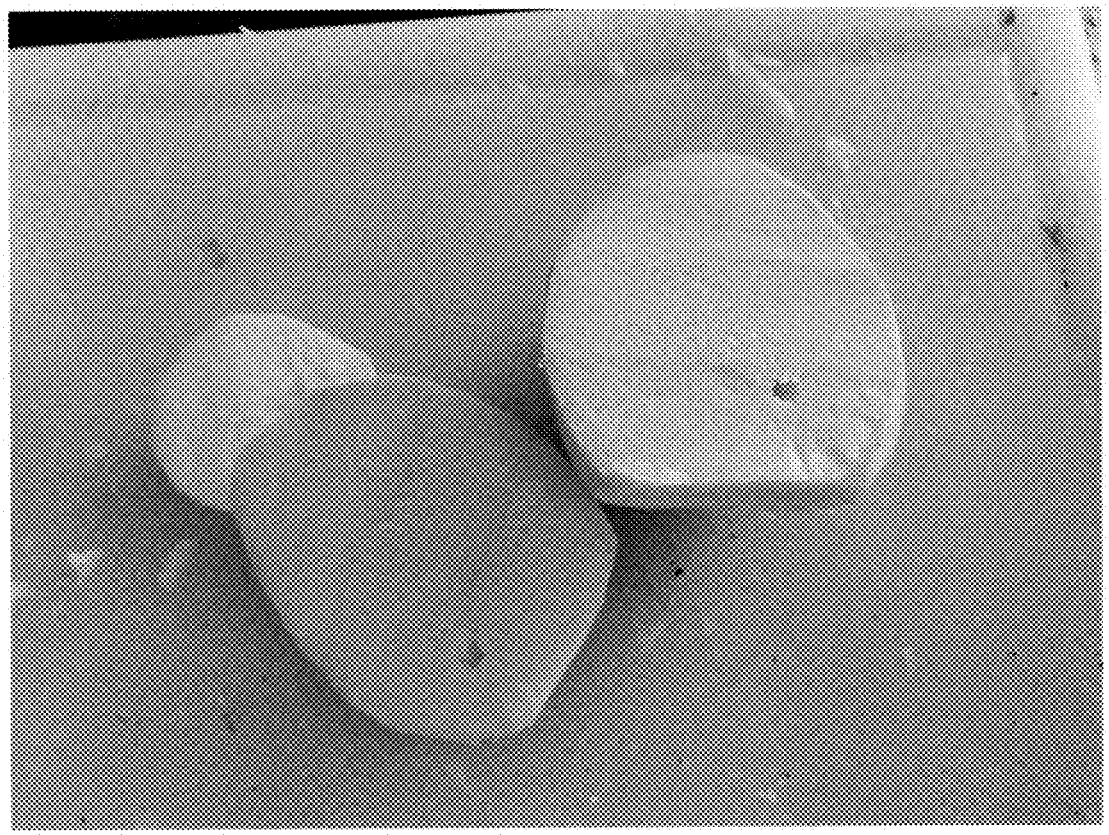
FIG. 17 and FIG. 18 show the mature flesh of the new variety 'Kankun'.
Figure 18:
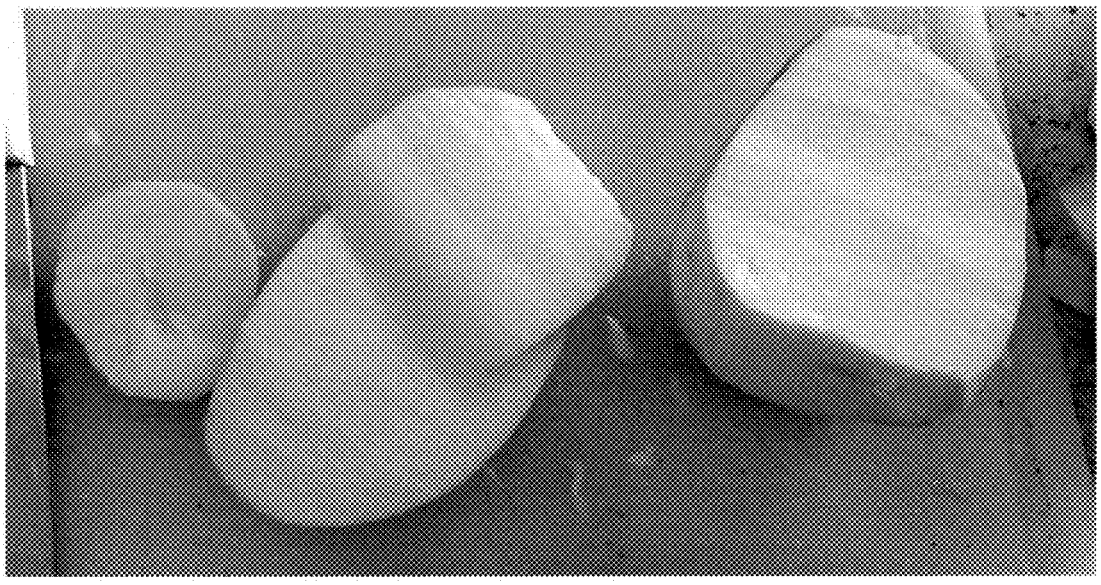

Throughout this specification, color names beginning with a small letter signify that the name of that color, as used in common speech, is aptly descriptive. Color names beginning with a capital letter designate values based upon The R.H.S. Colour Chart, published by Torso-Verlag, sixth edition, 2015.

The descriptive matter which follows pertains to 5-year-old 'Kankun' trees grown in Sinaloa, Mexico, observed during two agricultural cycles, 2017 to 2018 and 2018 to 2019, and is believed to apply to plants of the variety grown under similar conditions of soil and climate elsewhere.

TREE

General:

*Growth habit.*—Erect.
*Height.*—Approximately 3 m.
*Average spread.*—2 m to 2.5 m.
*Resistance and susceptibility to insects and pests.*—Tolerant to *Frankliniella occidentalis.*
*Plant hardiness.*—Tolerant to pH greater than 7 and electrical conductivity of 5.

Trunk:

*Surface texture.*—Striped.
*Color.*—About Greyed-White 156D.

FOLIAGE

Leaves:

*Length.*—Medium, approximately 31.19 cm.
*Width.*—Medium, approximately 5.3 cm.
*Ratio length/width.*—Medium, about 6.
*Leaf blade shape.*—Elliptical.
*Shape of Apex.*—Acuminate.
*Shape of base.*—Acute.
*Twisting.*—Absent.
*Margin.*—Medium ripple.
*Spacing of secondary veins.*—Medium.
*Shape in cross-section.*—Wide elliptical.
*Attitude in relation to shoot.*—Semi-erect and perpendicular.
*Pubescence in upper and lower surfaces.*—Absent.
*Color.*—Upper surface: About Green N134D. Lower surface: About Green 135B.
*Petiole length.*—Short, approximately 4.0 cm.
*Young leaf intensity of anthocyanin coloration.*—Strong.

FLOWERS

*Number of years to first flowering.*—4 years.
*Time of beginning of flowering.*—Early (January).
*Form.*—Pyramidal.
*Axis growth habit.*—Erect.
*Shape.*—Pyramidal.
*Length.*—Long, approximately 42 cm.
*Width.*—Approximately 37 cm.
*Diameter.*—Large.
*Ratio length/diameter.*—Small.
*Number of primary branches.*—Many.
*Peduncle color.*—Red.
*Peduncle diameter.*—Approximately 0.5 cm.
*Presence of leafy bracts.*—30.
*Anthocyanin coloration of the axis and branches.*—Strong.
*Petal size.*—Approximately 3 mm.
*Petal color.*—About Orange-Red 33C with crow-like brown spots.
*Sepal size.*—Approximately 2 mm.
*Petal color.*—About Brilliant Yellow Green 149A.

Reproductive organs:

*Hemaphrodite flower.*—Approximately 90%.
Color: About Yellow-Orange 14B.
*Male flower.*—Approximately 10%.
Color: About Brilliant Yellow Green 149A.

FRUIT

*Overall size.*—Medium.
*Time of fruit maturity.*—Early, in the month of May.
*Length.*—Medium, approximately 12.16 cm.

*Width.*—Medium.
*Weight.*—Approximately 440 g.
*Ratio length/width.*—Medium.
*Diameter at widest point.*—Approximately 9.52 cm.
*Shape in cross section.*—Broad elliptic.
*Ventral shoulder.*—Rounded upward.
*Dorsal shoulder.*—Rounded upward.
*Length of groove of ventral shoulder.*—Medium.
*Depth of groove of ventral shoulder.*—Medium.
*Bulging on ventral shoulder.*—Medium.
*Presence of sinus.*—Present.
*Depth of sinus.*—Medium.
*Point at stylar scar.*—Medium.
*Stalk cavity.*—Medium.
*Presence of neck.*—Present.
*Length of neck.*—Medium.
*Stalk length.*—Approximately 5 cm.
*Stalk diameter.*—Medium, approximately 0.3 cm.
*Stalk color.*—About Orange 28B.
*Beak.*—Absent.
*Skin texture.*—Smooth.
*Skin thickness.*—Medium.
*Skin color of immature fruit.*—About Green134A and Red 53A.
*Skin color of mature fruit.*—About Orange-Red N30C.
*Speckling of skin.*—Weak.
*Color contrast between lenticels and skin.*—Medium.
*Size of lenticels.*—Small.
*Skin texture.*—Smooth.
*Roughness of surface* (*corkiness caused by lenticels*).—Absent.
*Skin thickness.*—Medium.
*Adherence of skin to flesh.*—Medium.
*Flesh texture.*—Fine.
*Flesh color.*—About Yellow-Orange 17C.
*Flesh firmness.*—Medium.
*Juiciness.*—Medium.
*Flavor.*—Excellent.
*Turpentine flavor.*—Absent.
*Amount of fiber attached to skin.*—Low.
*Fiber.*—Limited.
*Fruit sugar content.*—17 brix.
*Storage quality.*—Quality is maintained in refrigeration at 12° C.
*Shelf life.*—Long, approximately 15 days.

STONE

*Color.*—Creme color.
*Average size.*—Approximately 9.4 cm by 4.9 cm.
*Venation.*—Ribbed.
*Texture of stone fiber.*—Fine fiber attached to the bone.
*Amount of fiber attached to stone.*—High.
*Relief of surface.*—Grooved.
*Shape of lateral view.*—Kidney-shaped.
*Susceptibility to bruising.*—None observed.
*Susceptibility to wind.*—None observed.
*Susceptibility to disease.*—None observed.
*Harvest date.*—Early (May to June).
*Heat tolerance.*—Tolerant to heat.

SEED

*Shape in lateral view.*—Reniform.
*Average size.*—Approximately 6.6 cm by 3.9 cm.
*Embryony.*—Polyembrionic.

What is claimed is:

1. A new and distinct variety of mango tree named 'Kankun' as herein described and illustrated.

* * * * *